United States Patent
Chauhan et al.

(10) Patent No.: US 7,635,493 B2
(45) Date of Patent: Dec. 22, 2009

(54) **HERBAL COMPOSITION FOR *TINEA* INFECTION**

(75) Inventors: Vijay Singh Chauhan, Maharashtra (IN); Kalkunte S. Satyan, Bangalore (IN); Kavita P. Kadam, Maharashtra (IN)

(73) Assignee: Piramal Life Sciences Limited, Maharashtra (IN)

(*) Notice: Subject to any disclaimer, the term of this patent is extended or adjusted under 35 U.S.C. 154(b) by 0 days.

(21) Appl. No.: 11/883,599

(22) PCT Filed: Jun. 17, 2005

(86) PCT No.: PCT/IB2005/051997

§ 371 (c)(1), (2), (4) Date: Sep. 7, 2007

(87) PCT Pub. No.: WO2006/082481

PCT Pub. Date: Aug. 10, 2006

(65) Prior Publication Data

US 2008/0113047 A1  May 15, 2008

(30) Foreign Application Priority Data

Feb. 2, 2005  (IN) .......... 101/MUM/2005

(51) Int. Cl.
*A61K 36/00* (2006.01)
(52) U.S. Cl. .................................. 424/725
(58) Field of Classification Search .............. None
See application file for complete search history.

(56) References Cited

U.S. PATENT DOCUMENTS

| | | | |
|---|---|---|---|
| 5,427,801 A * | 6/1995 | Uehara .............. 424/616 |
| 5,496,812 A * | 3/1996 | Platt .................. 514/171 |
| 6,180,669 B1 * | 1/2001 | Tamarkin ............ 514/548 |
| 6,254,897 B1 | 7/2001 | Shao |
| 6,583,164 B1 * | 6/2003 | Horibe et al. ........ 514/381 |
| 6,585,967 B2 * | 7/2003 | Narang et al. ....... 424/78.31 |
| 6,797,697 B2 * | 9/2004 | Seiberg et al. ....... 514/17 |
| 2002/0155138 A1 | 10/2002 | Martin et al. |
| 2004/0007284 A1 | 1/2004 | Look et al. |
| 2005/0175557 A1 * | 8/2005 | Mitra et al. ......... 424/59 |
| 2007/0065394 A1 * | 3/2007 | Pinney ............... 424/74 |

OTHER PUBLICATIONS

International Search Report for International Publication No. PCT/IB05/51997 dated Feb. 21, 2005.
Gupta et al., "Isolation of Ethyl *p*-Methoxycinnamate, the Major Antifungal Principle of Curcoma sedoaria", Lloydia. Jul.-Aug. 1976. vol. 39, No. 4. pp. 218-222.
Jansky et al., "Dynamics of Cytokine Production in Human Peripheral Blood Mononuclear Cells Stimulated by LPS or Infected by Borrelia" May 2003.
Plants For A Future: Database Search Results: *Hedychium spicatum*, 2000. 5 pages.
Website DREDDYCLINIC.com, Ayurvedic Herbs/Thai Herbs-Medicinal Plants-H, 2004, 6 pages.

* cited by examiner

*Primary Examiner*—Christopher R. Tate
(74) *Attorney, Agent, or Firm*—Hamre, Schumann, Mueller & Larson, P.C.

(57) ABSTRACT

Compositions containing extract of *hedychium spicatum* are useful for treating *Tinea* infections by topical application. Extracts from rhizomes of *hedychium spicatum* are particularly useful.

11 Claims, No Drawings

HERBAL COMPOSITION FOR *TINEA* INFECTION

FIELD OF THE INVENTION

The present invention relates to a novel herbal composition having anti-dermatophytic activity effective against *tinea* infections comprising plant substance as main ingredient, a method of manufacture and method of treating a patient having a *tinea* infection and the itching and inflammatory responses under such infective conditions. More particularly, the present invention relates to an anti-dermatophytic composition effective against *tinea* infections utilizing extract obtained from the plant *Hedychium spicatum*, containing ethyl p-methoxycinnamate as active ingredient, optionally in combination with other bioactive substances such as other anti-dermatophytes and melanogenesis inhibitors.

BACKGROUND OF THE INVENTION

The body normally serves as host for a variety of bacteria and fungi. Most of the time, the balance between the body as host and the microorganisms is maintained. Sometimes, however, conditions exist that permit the microorganisms to tip that balance, causing an infection.

Millions of people throughout the world are affected by superficial fungal infections, which are the most common skin diseases. These infections, which occur in both healthy and immunocompromised persons, are caused by dermatophytes, yeasts and nondermatophyte molds. Certain superficial fungal infections of the skin known as *tinea* infections are caused by dermatophytes, which are members of the *Trichophyton, Microsporum* and *Epidermophyton* species. These mold-like fungi thrive in warm, moist areas, thriving on the dead tissues of hair, nails, and outer skin layers. *Tinea* infections include *tinea capitis* which is fungal infection of the scalp that can cause hair loss; *tinea barbae* which is fungal infection in the beard; *tinea corporis* which is fungal infection of the skin other than beard, scalp, groin, hands or feet; *tinea cruris* which is fungal infection of the groin and perineum; *tinea pedis* which is fungal infection of the feet, known as athlete's foot; *tinea manuum* which is fungal infection of the hands and *tinea unguium* which is fungal infection of the nails. *Tinea* infections may result in lesions, which may be itchy. There may be deep inflammatory nodules. After the treatment, the dermal scars may remain, resulting in hyper and/or hypo pigmentation.

*Tinea* infections are contagious and can be passed through direct contact or by contact with clothing, from shower and pool surfaces, and even from pets. The estimated lifetime risk of acquiring a dermatophyte infection is between 10 and 20 percent.

Recognition and appropriate treatment of these infections reduces both morbidity and discomfort and lessens the possibility of transmission. The present line of treatment involves use of anti-fungals, such as tolnaftate, terbinafine hydrochloride, Griseofulvin and imidazoles such as ketoconazole, miconazole nitrate and clotrimazole. Griseofulvin is used for systemic therapy. Steroids are used with anti-fungals to control the inflammation. Common treatments using these anti-fungals require treatment two or three times a day for at least 10 to 14 days, and for some medications, for up to four weeks. Terbinafine hydrochloride taken in tablet form may have to be taken for considerable lengths of time, potentially for months. It is common treatment to apply the topical anti-fungal for two weeks after the skin is healed, to eradicate all remaining fungal spores. However topical application does not control dermatophytosis induced inflammation and dermal itch. Reoccurrences of the infection are frequent, and for some patients, such as those who suffer from diabetes or circulatory problems, *tinea* infections and their treatment can be quite serious. The present line of treatment is expensive and has common side effects such as hepatotoxicity, nausea, diarrhea and impotency. Long term use and misuse of these drugs will result in development of drug resistance by the organisms.

Methods for reducing side effects of treatments include use of herbal compositions. Herbs have long been known and used throughout the world for treatment of many conditions, including skin conditions, and there is at least some evidence that herbal remedies may tend to have less deleterious side effects than corresponding synthetic drugs. Even with herbal treatments, however, numerous difficulties are encountered in the treatment of medical conditions. A single herb may contain numerous active, and sometimes conflicting, components. Herbs, such as black walnut extract which is used to treat athlete's foot, related fungal infections and cancers, as well as to lower blood pressure and cholesterol can be toxic. Additional potential difficulties arise from plant-to-plant variation in the concentration and efficacy of active components. Such difficulties are considerably exacerbated with respect to herbal compositions. Combinations raise the possibility of synergistic effects among components in the various herbs. Though this has advantages it can also increase the difficulties associated with anticipating and analyzing side effects.

So, it is important to ascertain the effects/side effects of the herbal extract by establishing the presence and characterization of the active ingredient.

Many herbs are reported to have substantial effects on skin ailments. Herbs within this group include, for example *Angelicae pubescentis Radix* for treatment of psoriasis. Herbs traditionally known or used for treating athlete's foot specifically include tea tree, garlic, goldenseal and various parts of the black walnut tree, which is known to be toxic.

Combinations of herbs are also known to have substantial effects on skin ailments. For example, one herbal treatment for *tinea* infections uses herbal extracts from Aloe vera, Chicory root, Catnip, St. John's wort and vitamins A and E, in a cream base. This treatment is recommended for application 3 to 4 times daily for 2 to 3 days after all lesions are healed.

U.S. Pat. No. 6,254,897 describes a composition effective against *tinea* infections utilizing natural substances obtained from a combination of *Angelicae pubescentis Radix, Notopterygium Radix* and *Haliotis diversicolor* Reeve. The drawbacks of this composition are— a. It is mixture of three or more plant extracts. So, one has to collect or cultivate these plants.
  b. These plants are not described in traditional medicine for anti- *tinea* activity, hence may need detailed studies to establish safety.
  c. The patent does not contain information regarding the active ingredient present in the plant extract/s, which is responsible for anti- *tinea* activity.
  d. The patent does not contain information regarding the synergistic effect of the plant extracts used.

Hence there is a need to develop a new composition, which can overcome the above mentioned problems associated with the synthetic preparations or herbal extracts used at present, for the treatment of *tinea* infections.

*Hedychium spicatum*, is a plant which grows naturally in subtropical regions such as India and China, where it is used as a traditional medicine. It is also cultivated in various parts of the world for its fragrant rhizome. Traditional indications for the use of *Hedychium spicatum*, include stomactic, indegestion, calmative, bitter tonic, expectorant, liver disorders, hair growth promoter, anti-bacterial, anti-fungal, anti-inflammatory and anti-malarial (US Patent Publication No. 20020155138). One of the chemical constituents present in *Hedychium spicatum*, is ethyl p-methoxycinnamate which is reported to be anti-dermatophytic (Lloydia, 39(4), 218-222, (1976)).

However there is no report of any composition containing *Hedychium spicatum* for dermatophytic treatment. To overcome the problems of side effects of present line of treatment and to reduce the cost of treatment the present inventors prepared a novel herbal composition having anti-dermatophytic activity effective against *tinea* infections and against the itching and inflammatory responses under such infective conditions, utilizing extract obtained from the plant *Hedychium spicatum*, containing effective amount of ethyl p-methoxycinnamate as active ingredient, optionally in combination with other bioactive substances such as other anti-dermatophytes and melanogenesis inhibitor. Additionally, the composition possesses natural deodorant properties.

SUMMARY OF THE INVENTION

Accordingly, it is an object of the present invention to provide a herbal composition containing extract of *Hedychium spicatum*, containing effective amount of active ingredient ethyl p-methoxycinnamate, for treatment of *tinea* infections.

Another object of the present invention is directed at making and utilizing a composition containing a safe and effective amount of *Hedychium spicatum*, for treatment of *tinea* infections.

Another object of the present invention is to deliver a unique herbal composition with Tumor Necrosis Factor-alpha (TNF-α) inhibition, which would reduce the dermal itch and inflammation associated with the *tinea* infections.

Yet another objective of the invention is to disclose the use of such products alone or in combination with melanogenesis inhibitors to control the post-infection dermal scars.

Yet another object of the present invention is to provide a composition for treating *tinea* infections quickly and effectively.

Other objects and further scope of applicability of the present invention will become apparent from the detailed description to follow. It should be understood, however, that the detailed description and specific examples, while indicating embodiments of the invention, are given by way of illustration only, since various changes and modifications within the spirit and scope of the invention will become apparent to those skilled in the art.

DETAILED DESCRIPTION OF THE INVENTION

One skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs.

As used herein, "topical application" means directly laying on or spreading on outer skin using, e.g., by use of the hands or an applicator such as a wipe. As used herein, "safe and effective amount" means an amount of compound or composition (e.g., the *Hedychium spicatum* extract) sufficient to significantly induce a positive modification in the condition to be regulated or treated, but low enough to avoid serious side effects (at a reasonable benefit/risk ratio), within the scope of sound medical judgment. The safe and effective amount of the compound or composition will vary with the particular condition being treated, the age and physical condition of the end user, the severity of the condition being treated/prevented, the duration of the treatment, the nature of concurrent therapy, the specific compound or composition employed, the particular cosmetically-acceptable carrier utilized, and like factors.

As used herein, all percentages are by weight unless otherwise specified.

"*Hedychium spicatum* extract" mentioned here means a blend of compounds present in plant *Hedychium spicatum*. Such compounds may be extracted from the dried rhizome of the plant using extraction procedures well known in the art (e.g., the use of organic solvents such as lower alcohols, alkyl esters, alkyl ethers, alkyl ketones, chloroform, petroleum ether, hexane and/or inorganic solvents such as water). In one embodiment, the *Hedychium spicatum* extract contains only hydrophobic compounds (e.g. isolated by using a hydrophobic solvent, such as chloroform, petroleum ether, hexane). One of the hydrophobic compounds referred is the active ingredient ethyl p-methoxycinnamate. The extract preferably contains effective amount (4-10%) of ethyl p-methoxycinnamate, which can be estimated using conventional assay techniques such HPTLC or HPLC.

This extract is then used to prepare topical preparations containing 0.1-20% by weight of the rhizome extract, preferably from about 2.5-10% (w/w), which is thoroughly blended into a conventional base as will be hereafter described in detail. It is to be noted that for most of the conditions targeted, rhizome extract having 4-10% (w/w) of ethyl p-methoxycinnamate, preferably 6-8% (w/w) as active ingredient, is sufficient to achieve the desired results.

The topical compositions useful in the present invention involve formulations suitable for topical application to skin. The compositions may be formulated in to into a wide variety of product types that include but are not limited to lotions, creams, gels, sticks, sprays, ointments, cleansing liquid washes and solid bars, shampoos, pastes, mousses, wipes, patches, wound dressing and adhesive bandages, hydrogels, films- and cosmetics.

In formulating the ultimate composition, a number of traditional ingredients may be used. For instance, water; lanolin; vaseline; glycerol; triglycerides of fatty acids; polyethylene glycols; oxyethyleneated fatty alcohols; esters such as isopropyl palmitate; myristate and stearate; silicone oils; oleyl oleate and butyl stearate; animal, vegetable, or mineral oils; fatty alcohols; glycerol monostearate, and organic and mineral waxes. These ingredients are generally used in an amount of about 10% to 97% by weight of the total formulation and can be either a single or a multiple phase system.

One of the products that may be formulated is a cream. A cream typically comprises from about 5% to about 50% (e.g., from about 10% to about 20%) of an emollient(s) and from about 45% to about 85% (e.g., from about 50% to about 75%) of water.

Another type of product that may be formulated is an ointment. An ointment may comprise a simple base of animal or vegetable oils or semi-solid hydrocarbons. Ointments may also comprise absorption ointment bases that absorb water to form emulsions. An ointment may comprise from about 2% to about 60% of an emollient(s) plus from about 2% to about 60% of a thickening agent(s).

The topical compositions of the present invention can also be formulated into a solid formulation (e.g., a wax-based stick or soap bar composition). In another embodiment, the topical composition further comprises another plant extract exhibiting anti-dermatophytic activity in addition to the *Hedychium spicatum* extract to obtain the synergistic effect. Plant may be selected from plants such as *Curcuma zedoaria, Kaempferia galanga, Angelicae pubescentis Radix, Notopterygium Radix* and *Haliotis diversicolor* Reeve for extraction.

In yet another embodiment, the topical composition further comprises another synthetic compound exhibiting anti-dermatophytic activity in addition to the *Hedychium spicatum* extract to obtain a synergistic effect. Synthetic compounds may be selected from the anti-fungals, such as Griseofulvin, tolnaftate, and terbinafine hydrochloride and imidazoles such as miconazole nitrate and clotrimazole.

In yet another embodiment, the topical composition further comprises other natural melanogenesis inhibitors, which can provide blemish free skin post-infection, in addition to the *Hedychium spicatum* extract to obtain the synergestic effect. Natural melanogenesis inhibitor may be selected from licorice, glabradin, glabrene, arbutin, curcumin, ellagic acid, pomegranate extract.

The compositions of the present invention are suitable for use in the treatment of both acute and chronic forms of *tinea* infections, in particular the infections caused by *Trichophyton, Epidermophyton* and *Microsporum* species, in healthy and immunocompromised humans. The compositions of the present invention have following additional advantages— a. the anti-inflammatory activity of the extract and active ingredient ethyl p-methoxycinnamate because of which both inflammation and itching associated with *tinea* infection are controlled.

b. the natural deodorant property of the extract which will reduce the bad odor associated with certain *tinea* infections.

EXAMPLE 1

Preparation of Extract of *Hedychium spicatum*

Dried *Hedychium spicatum* rhizome (100 g) was pulverized. The powdered material was extracted using chloroform (500 mL) by refluxing at 60° C. for 3 hrs. The extract was filtered under vacuum. This extraction process was repeated two more times. The extracts were combined and concentrated to remove the solvent.

Yield: 2.5 g Ethyl p-methoxycinnamate content in the extract (estimated by HPTLC): 6.5% (w/w).

EXAMPLE 2

Isolation of Ethyl p-methoxycinnamate

Powdered *Hedychium spicatum* rhizome (5 kg) was extracted using hexane by stirring at 60° C. for 1 h. The extract was filtered under vacuum. This extraction process was repeated two more times. The combined filtrates were evaporated to dryness to obtain the crude extract. Yield: 134 g.

The crude extract (100 g) was purified by column chromatography (silica gel, pet ether in ethylacetate) to obtain ethyl p-methoxycinnamate. Final purification was achieved by crystallization using pet ether.

Yield: 3.5 g; mp 48-50° C.; $^1$H NMR (CDCl$_3$, 300 MHz): δ 1.33 (t, 3H, CH$_3$), 3.83 (s, 3H, OCH$_3$), 4.26 (q, 2H, CH$_2$), 6.28 (s, 1H), 6.33 (s, 1H), 6.88 (m, 3H), 7.46 (d, 1H); MS: m/e (EI) 206 (M+).

EXAMPLE 3

Anti-TNFα Activity of the *Hedychium spicatum* Extract and Lead Molecule

Assay for Screening in Human Peripheral Blood Mononuclear Cells (hPBMCs).

TNF-α production by Lipopolysaccharide (LPS) in hPBMC was measured according to the method described by Jansky, L. et al (Physiol. Res. 52, 593-598, (2003)). Blood was collected from healthy donors into vacutainer tubes coated with potassium EDTA (Vacutest Plast) and diluted 1:2 with Dulbecco's Phosphate Buffered Saline (DPBS) (Sigma Aldrich, St. Louis, Mo.). The PBMC were harvested from human blood and suspended in RPMI 1640 culture medium (Gibco BRL, Pasley, UK) containing 10% fetal bovine serum (FBS) (Hyclone, Utah, USA), 100 U/ml penicillin (Sigma Chemical Co. St Louis, Mo.) and 100 µg/ml streptomycin (Sigma Chemical Co. St Louis, Mo.). The cell concentration was adjusted to 1×10$^6$ cells/ml. The cell suspension (100 µl) was added to the wells of a 96-well culture plate. Following cell plating, 79 µl of the culture medium and 1 µl of eight different concentrations of the test samples (10 to 100 µg/ml) dissolved in dimethylsulfoxide (DMSO, Sigma, Mo., USA) were added to the cells. The final concentration of DMSO was adjusted to 0.5-1%. Rolipram (100 µM) was used as a standard compound. The plates were incubated for 30 min at 37° C. in an atmosphere of 5% CO$_2$. Finally, 20 µl (10 µg/ml) per well of LPS, (*Escherchia coli* 0127:B8, Sigma Chemical Co., St. Louis, Mo.) was added, to obtain a final concentration of 2 µg/ml. The plates were incubated at 37° C. for 5 h in an atmosphere of 5% CO$_2$. Supernatants were harvested and assayed for % TNF-α inhibition by ELISA as described by the manufacturer (R&D Systems, MN) or by cytotoxicity bioassay in L929 cells.

Results: TNF-α inhibition of *Hedychium spicatum* extract and lead molecule (ethyl p-methoxycinnamate) in Human polymorph nuclear cells are shown in table 1.

TABLE 1

TNF alpha inhibition in human polymorph nuclear cells.

| Sample | Concentration (µg/ml) | % TNF-α Inhibition |
|---|---|---|
| Extract of Example 1 | 10 | 5 |
| Extract of Example 1 | 100 | 96 |
| Ethyl p-methoxycinnamate | 10 | 0 |
| Ethyl p-methoxycinnamate | 100 | 80 |

Conclusion: Extract of *Hedychium spicatum* and the lead molecule (ethyl p-methoxycinnamate) inhibit TNF alpha activity.

Results: Cytotoxicity of *Hedychium spicatum* extract and lead molecule (ethyl p-methoxycinnamate) in L929 cell lines is given in table 2.

TABLE 2

Cytotoxicity in L929 cell lines.

| Sample | Concentration (µg/ml) | 3.5 h | 24 h |
|---|---|---|---|
| Extract of Example 1 | 10 | 00 | 05 |
| Extract of Example 1 | 100 | 03 | 14 |
| Ethyl p-methoxycinnamate | 10 | 20 | 27 |
| Ethyl p-methoxycinnamate | 100 | 12 | 02 |

Conclusion: Extract of *Hedychium spicatum* and the lead molecule (ethyl p-methoxycinnamate) exhibit low cytotoxicity as measured in L929 cell lines.

EXAMPLE 4

Preparation of Ointment Formulation

General Procedure.

Weigh and transfer all the ingredients 01 to 05 (refer to table 3) in the specified quantity, to a suitable vessel. Melt the ingredients using water bath and mix well. Add *Hedychium spicatum* extract of Example 1 in specified quantity to the above blend and mix well in a homogenizer. Cool the contents uniformly under stirring to obtain the ointment.

Results: Formulations containing 2.5, 5 and 10% of *Hedychium spicatum* extract are given in table 3.

TABLE 3

Ointment Formulation of *Hedychium spicatum*.

| No. | INGREDIENT | Ointment I % W/W | Ointment II % W/W | Ointment III % W/W |
|---|---|---|---|---|
| 01 | White Bees Wax | 5.00 | 5.00 | 4.50 |
| 02 | Hard Paraffin | 13.50 | 9.50 | 9.50 |
| 03 | Microcrystalline Wax | 9.00 | 9.50 | 9.50 |
| 04 | White Soft Paraffin | 50.00 | 52.00 | 55.00 |
| 05 | Light Liquid Paraffin | 12.50 | 19.00 | 19.00 |
| 06 | Extract of Example 1 | 10.00 | 5.00 | 2.50 |
|  | Total | 100.00 | 100.00 | 100.00 |

EXAMPLE 5

Preparation of Cream Formulation

General Procedure.

Weigh and transfer the ingredients 01, 02, 03 and 05 (refer to table 4) in the specified quantity, as per the batch size, to a suitable vessel. Melt the ingredients using water bath and mix well. Add ingredient 07 (*Hedychium spicatum* extract of Example 1) in specified quantity to the above blend and mix well. Weigh and dissolve ingredient 04 in 06 and add to the above blend and mix well to obtain the cream.

Results: Formulations containing 2.5, 5 and 10% of *Hedychium spicatum* extract are given in table 4.

TABLE 4

Cream Formulation of *Hedychium spicatum*.

| No. | INGREDIENT | Cream I % W/W | Cream II % W/W | Cream III % W/W |
|---|---|---|---|---|
| 01 | White Soft Paraffin | 18.00 | 17.27 | 17.73 |
| 02 | Light Liquid Paraffin | 7.20 | 6.91 | 7.09 |
| 03 | Cetostearyl Alcohol | 9.72 | 9.33 | 9.57 |
| 04 | Sodium Lauryl Sulfate | 1.08 | 1.04 | 1.06 |
| 05 | Phenoxyethanol | 0.90 | 0.86 | 0.89 |
| 06 | Water | 53.10 | 59.59 | 61.16 |
| 07 | Extract of Example. 1 | 10.00 | 5.00 | 2.50 |
|  | Total | 100.00 | 100.00 | 100.00 |

EXAMPLE 6

Anti-dermatophytic Activity of Formulations

In vitro Assay Procedure.

Organisms: *Trichophyton mentagrophytes* & *Microsporum gypseum*.

Inoculum Preparation.

Cultures were grown on PDA agar slants at 28° C. for 7 days. The growth was covered with sterile saline & scraped to get a growth suspension. The resulting mixture of conidia or sporangiospores & hypal fragments was transferred to a sterile test tube. The heavy particles were allowed to settle & upper homogenous suspension was transferred to another tube. These suspensions were adjusted to an optical density that ranged from 0.09 to 0.11 (80 to 82% transmittance) using a spectrophotometer. These stock suspensions were further diluted 1:10 with saline to obtain test inoculum ($1 \times 10^3$ to $5 \times 10^3$ cfu/ml).

Sample-preparation.

Ointment & Cream: A 100 mg/ml stock solution of ointment & cream of example 4 and 5 was prepared in demineralised water+0.01% Tween 20. Calculated amount of stock solution was added to 20 ml of Sabarouds melted agar medium & poured into petri plates so as to get a series of serial two fold dilution of the extract in the medium. Five concentrations of 100, 50, 25, 10 & 5 mg/ml were used for both formulations in initial study. A repeated study was carried out using lower concentrations of both the formulations. The concentrations used were 5, 1, 0.9, 0.8, 0.7, 0.6, 0.5, 0.4 0.3, 0.2 & 0.1 mg/ml.

Extract of Example 1 and Ethyl p-methoxycinnamate:

Concentrations of 0.01 to 0.10 mg/ml were prepared by the above described method.

A growth control plate without any extract or formulation was included in the study.

Marketed samples of Ketoconazole (2%) in 0.5 mg/ml concentration and Tolnaftate (1%) in 0.05 mg/ml concentration were used as standards for comparison.

Assay.

The culture suspensions prepared by above method were spotted in 10 μl amount on the solidified plates. Spots were allowed to dry at room temperature & then the plates were incubated at 28° C./48 h.

End Point Criteria.

The MIC was defined as the lowest concentration of extract or formulation giving no visible growth or causing almost complete inhibition of growth in the plates. Results are given in table 5.

TABLE 5

In vitro anti-dermatophytic activity of the formulations

| | | MIC (mg/ml) | |
|---|---|---|---|
| No. | Sample | T. mentagrophytes | M. gypseum |
| 1 | Ointment I* | 1 | 1 |
| 2 | Ointment II* | 5 | 5 |
| 3 | Ointment III* | 5 | 5 |
| 4 | Cream I** | 0.5 | 0.5 |
| 5 | Cream II** | 1 | 1 |
| 6 | Cream III** | 5 | 5 |

TABLE 5-continued

In vitro anti-dermatophytic activity of the formulations

| | | MIC (mg/ml) | |
|---|---|---|---|
| No. | Sample | T. mentagrophytes | M. gypseum |
| 7 | Extract of Example 1 | 0.04 | 0.04 |
| 8 | Ethyl p-methoxycinnamate | 0.03 | 0.03 |
| 9 | Ketoconazole (2%)** | 0.5 | 0.5 |
| 10 | Tolnaftate(1%)** | 0.05 | 0.05 |

*of Example 4.
**of Example 5.
**Topical anti-dermatophytic preparation.

Conclusions:
1. Cream and the ointment formulations containing *Hedychium spicatum* extract exhibit anti-dermatophytic activity.
2. Cream exhibits better anti-dermatophytic activity compared to the ointment.
3. Cream containing 10% *Hedychium spicatum* extract exhibits anti-dermatophytic activity comparable with marketed sample of topical anti-dermal preparation containing Ketoconazole (2%).

Main Advantages of Present Composition:
1. The composition will be effective in reducing the itching and the inflammation associated with the *tinea* infection.
2. The composition will have natural deodorant property, which is useful for treating tinea infection with bad odor.

We claim:

1. A method of treating *tinea* infection in a patient suffering therefrom, said method comprising topical application to the patient of an herbal composition, comprising an effective amount of an extract of the plant, *Hedychium spicatum* and a pharmaceutically acceptable carrier.

2. The method of claim 1, wherein said composition comprises an extract of the rhizomes of the plant, *Hedychium spicatum*.

3. The method of claim 1, wherein the *tinea* infection is caused by *Trichophyton mentagrophytes*.

4. The method of claim 1, wherein the *tinea* infection is caused by *Microsporum gypseum*.

5. The method of claim 1, wherein said extract provided in the composition is in an amount of 0.1% -20% by weight.

6. The method of claim 5, wherein said extract provided in the composition is in an amount of 2.5% to 10% by weight.

7. The method of claim 5, wherein said extract in the composition comprises an effective amount of ethyl p-methoxy cinnamate as an active ingredient.

8. The method of claim 7, wherein the ethyl p-methoxy cinnamate present in the composition is in an effective amount of 4% to 10% by weight.

9. The method of claim 8, wherein the ethyl p-methoxy cinnamate is present in an amount of 6% to 8% by weight.

10. The method of claim 1, wherein said composition is in the form of an ointment.

11. The method of claim 1, wherein said composition is in the form of a cream.

* * * * *